(12) United States Patent
Steinhoff

(10) Patent No.: US 10,370,714 B2
(45) Date of Patent: Aug. 6, 2019

(54) TH-17 DIFFERENTIATION MARKERS FOR ROSACEA AND USES THEREOF

(75) Inventor: Martin Steinhoff, San Francisco, CA (US)

(73) Assignees: GALDERMA RESEARCH & DEVELOPMENT, Biot (FR); UNIVERSITAT MUNSTER, Munster (DE)

( * ) Notice: Subject to any disclaimer, the term of this patent is extended or adjusted under 35 U.S.C. 154(b) by 1023 days.

(21) Appl. No.: 14/129,679

(22) PCT Filed: Jun. 25, 2012

(86) PCT No.: PCT/EP2012/062259
§ 371 (c)(1), (2), (4) Date: Apr. 10, 2014

(87) PCT Pub. No.: WO2013/000871
PCT Pub. Date: Jan. 3, 2013

(65) Prior Publication Data
US 2014/0221231 A1 Aug. 7, 2014

Related U.S. Application Data

(60) Provisional application No. 61/501,369, filed on Jun. 27, 2011.

(51) Int. Cl.
C12Q 1/68 (2018.01)
C12Q 1/6883 (2018.01)

(52) U.S. Cl.
CPC ..... *C12Q 1/6883* (2013.01); *C12Q 2600/158* (2013.01)

(58) Field of Classification Search
None
See application file for complete search history.

(56) References Cited

FOREIGN PATENT DOCUMENTS

| WO | 2007/003915 A1 | 1/2007 | |
|----|----------------|--------|---|
| WO | 2010/049144 A2 | 5/2010 | |
| WO | WO 2010049144 A2 * | 5/2010 | ........... A61K 31/192 |
| WO | 2011/014775 A1 | 2/2011 | |
| WO | 2011/073321 A1 | 6/2011 | |

OTHER PUBLICATIONS

NCBI Accession No. NM_001001523 (Dec. 1999).*
Villey et al. (RORgammaT, a thymus-specific isoform of the orphan nuclear receptor RORgamma / TOR, is up-regulated by signaling through the pre-T cell receptor and binds to the TEA promoter, Eur J Immunol. Dec. 1999;29(12):4072-80).*
Ivanov et al. (The orphan nuclear receptor RORgammat directs the differentiation program of proinflammatory IL-17+ T helper cells, Cell. Sep. 22, 2006;126(6):1121-33).*

(Continued)

*Primary Examiner* — Aaron A Priest
(74) *Attorney, Agent, or Firm* — Sunit Talapatra; Foley & Lardner LLP

(57) ABSTRACT

A method is described that uses ROR gamma t, or ROR alpha to diagnose rosacea and/or to screen inhibitors of Th17 differentiation, notably in inhibiting ROR gamma t or ROR alpha. Also described is a method of using these screened inhibitors in rosacea treatment.

11 Claims, 2 Drawing Sheets

| GENE_SYMBOL | TITLE | Healthy volunteers Mean_Expressions | patients with Rosacea type I Mean_Expression | patients with Rosacea type I vs Healthy volunteers Fold_Change | patients with Rosacea type I vs Healthy volunteers Adjusted Pvalue | patients with Rosacea type II Mean_Expression | patients with Rosacea type II vs Healthy volunteers Fold Change | patients with Rosacea type II vs Healthy volunteers Adjusted Pvalue | patients with Rosacea type III Mean_Expression | patients with Rosacea type III vs Healthy volunteers Fold Change | patients with Rosacea type III vs Healthy volunteers Adjusted Pvalue |
|---|---|---|---|---|---|---|---|---|---|---|---|
| IL26 | interleukin 26 | 12 | 48 | 4,1 | 6,7E-05 | 259 | 22,5 | 3,2E-09 | 80 | 6,9 | 2,5E-06 |
| CCL20 | chemokine (C-C motif) ligand 20 | 46 | 183 | 4,0 | 9,8E-05 | 259 | 5,5 | 1,2E-05 | 256 | 5,5 | 1,3E-05 |
| IL22 | interleukin 22 | 7 | 11 | 1,5 | 3,7E-01 | 24 | 3,4 | 1,3E-02 | 11 | 1,6 | 3,7E-01 |
| IL17A | interleukin 17A | 7 | 8 | 1,2 | 5,7E-01 | 18 | 2,7 | 3,0E-04 | 13 | 1,9 | 1,4E-02 |
| IL6 | interleukin 6 (interferon, beta 2) | 14 | 15 | 1,1 | 7,0E-01 | 34 | 2,5 | 2,0E-04 | 21 | 1,6 | 4,4E-02 |
| TNF | tumor necrosis factor | 40 | 52 | 1,3 | 3,2E-02 | 88 | 2,2 | 1,7E-06 | 67 | 1,7 | 2,0E-04 |
| RORC | RAR-related orphan receptor C | 245 | 205 | -1,2 | 3,1E-01 | 105 | -2,3 | 5,8E-05 | 105 | -2,3 | 5,3E-05 |
| RORA | RAR-related orphan receptor A | 7858 | 4104 | -1,9 | 1,4E-06 | 2634 | -3,0 | 1,8E-09 | 3375 | -2,3 | 6,9E-08 |
| IL5 | interleukin 5 (colony-stimulating factor, eosinophil) | No detected | No detected | | | No detected | | | No detected | | |
| IL4 | interleukin 4 | 8 | 7 | -1,1 | 1,8E-01 | 8 | -1,1 | 2,8E-01 | 7 | -1,1 | 2,6E-02 |
| IL13 | interleukin 13 | 41 | 42 | 1,0 | 7,2E-01 | 40 | -1,0 | 9,3E-01 | 38 | -1,1 | 2,9E-01 |

(56) References Cited

OTHER PUBLICATIONS

Miossec et al. (IL-17 and Th17 cells in human inflammatory diseases, Microbes Infect. Apr. 2009;11(5):625-30. doi: 10.1016/j.micinf.2009.04.003. Epub Apr. 14, 2009).*

Manel et al. (The differentiation of human T(H)-17 cells requires transforming growth factor-beta and induction of the nuclear receptor RORgammat, Nat Immunol. Jun. 2008;9(6):641-9. doi: 10.1038/ni.1610. Epub May 4, 2008).*

Schambach et al. (Activation of retinoic acid receptor-alpha favours regulatory T cell induction at the expense of IL-17-secreting T helper cell differentiation, Eur J Immunol. Sep. 2007;37(9):2396-9).*

Yamasaki et al. (TLR2 expression is increased in rosacea and stimulates enhanced serine protease production by keratinocytes, J Invest Dermatol. Mar. 2011;131(3):688-97. doi: 10.1038/jid.2010.351. Epub Nov. 25, 2010).*

American Academy of Dermatology, Rosacea, available at https://www.aad.org/public/diseases/acne-and-rosacea/rosacea, accessed Nov. 26, 2018.*

International Search Report dated Dec. 3, 2012 by the European Patent Office as the International Searching Authority in corresponding International Patent Application No. PCT/EP2012/062259, 7 pages.

Martinez, G. J., et al., "Regulation and Function of Proinflammatory TH17 Cells," Annals of the New York Academy of Sciences, vol. 1143, No. 1, Nov. 1, 2008, pp. 188-211.

Ikeda, U., et al., "1alpha, 25-Dihydroxyvitamin D3 and all-trans retinoic acid synergistically inhibit the differentiation and expansion of Th17 cells," Immunilogy Letters, vol. 134, No. 1, Nov. 30, 2010, pp. 7-16.

Yamasaki, K., et al., "The molecular pathology of rosacea," Journal of Dermatological Science, Elsevier Science Publishers, vol. 55, No. 2, Aug. 1, 2009, pp. 77-81.

* cited by examiner

FIG. 1

| GENE_SYMBOL | TITLE | Healthy volunteers Mean_Expressions | patients with Rosacea type I Mean_Expression | patients with Rosacea type I vs Healthy volunteers Fold_Change | patients with Rosacea type I vs Healthy volunteers Adjusted_Pvalue | patients with Rosacea type II Mean_Expression | patients with Rosacea type II vs Healthy volunteers Fold_Change | patients with Rosacea type II vs Healthy volunteers Adjusted_Pvalue | patients with Rosacea type III Mean_Expression | patients with Rosacea type III vs Healthy volunteers Fold_Change | patients with Rosacea type III vs Healthy volunteers Adjusted_Pvalue |
|---|---|---|---|---|---|---|---|---|---|---|---|
| IL26 | interleukin 26 | 12 | 48 | 4,1 | 6,7E-05 | 259 | 22,5 | 3,2E-09 | 80 | 6,9 | 2,5E-06 |
| CCL20 | chemokine (C-C motif) ligand 20 | 46 | 183 | 4,0 | 9,8E-05 | 259 | 5,6 | 1,2E-05 | 256 | 5,5 | 1,3E-05 |
| IL22 | interleukin 22 | 7 | 11 | 1,5 | 3,7E-01 | 24 | 3,4 | 1,3E-02 | 11 | 1,6 | 3,7E-01 |
| IL17A | interleukin 17A | 7 | 8 | 1,2 | 5,7E-01 | 18 | 2,7 | 3,0E-04 | 13 | 1,9 | 1,4E-02 |
| IL6 | interleukin 6 (interferon, beta 2) | 14 | 15 | 1,1 | 7,0E-01 | 34 | 2,5 | 2,0E-04 | 21 | 1,6 | 4,4E-02 |
| TNF | tumor necrosis factor | 40 | 52 | 1,3 | 3,2E-02 | 88 | 2,2 | 1,7E-06 | 67 | 1,7 | 2,0E-04 |
| RORC | RAR-related orphan receptor C | 245 | 205 | -1,2 | 3,1E-01 | 105 | -2,3 | 5,6E-05 | 105 | -2,3 | 5,3E-05 |
| RORA | RAR-related orphan receptor A | 7858 | 4104 | -1,9 | 1,4E-06 | 2634 | -3,0 | 1,8E-09 | 3375 | | 6,9E-08 |
| IL5 | interleukin 5 (colony-stimulating factor, eosinophil) | No detected | No detected | | | No detected | | | No detected | | |
| IL4 | interleukin 4 | 8 | 7 | -1,1 | 1,8E-01 | 8 | -1,1 | 2,8E-01 | 7 | -1,1 | 2,6E-02 |
| IL13 | interleukin 13 | 41 | 42 | 1,0 | 7,2E-01 | 40 | -1,0 | 9,3E-01 | 38 | -1,1 | 2,9E-01 |

FIG. 2

| protein | | | Rosacea subtype 1 | Rosacea subtype 2 | Healthy skin | Rosacea subtype 1 / Healthy | | Rosacea subtype 2 / Healthy | |
|---|---|---|---|---|---|---|---|---|---|
| Symbol | Name | Primary accession N° | conc. [pg/mg] | conc. [pg/mg] | conc. [pg/mg] | Fold modulation | p-value | Fold modulation | p-value |
| IL-22/IL-TIF | Interleukin-22 | Q9GZX6 | 20,7 | 22,1 | 11,0 | 1,9 | <0,05 | 2,0 | <0,05 |
| MIP-3alpha/CCL20 | C-C motif chemokin | P78556 | 1,6 | 1,2 | 0,7 | 2,2 | <0,01 | 1,6 | <0,05 |
| IL-17F/ML-1 | Interleukin-17F | Q96PD4 | 1,7 | 1,4 | 0,9 | 1,9 | <0,01 | 1,5 | <0,01 |
| Il-4 | Interleukin-4 | P05112 | blq | blq | blq | blq | NS | blq | NS |
| Il-5 | Interleukin-5 | P05113 | 1,0 | 0,9 | 0,8 | 1,2 | NS | 1,1 | NS |
| Il-13 | Interleukin-13 | P35225 | 7,4 | 3,8 | 3,0 | 2,5 | NS | 1,3 | NS |

TH-17 DIFFERENTIATION MARKERS FOR ROSACEA AND USES THEREOF

CROSS-REFERENCE TO PRIOR APPLICATIONS

This application is a National Stage of PCT/EP2012/062259, filed Jun. 25, 2012, and designating the United States (published in English on Jan. 3, 2013, as WO 2013/000871 A1), which claims priority under 35 U.S.C. § 119 to U.S. Provisional Patent Application 61/501,369, filed Jun. 27, 2011, each hereby expressly incorporated by reference in its entirety and each assigned to the assignee hereof.

The invention is related to a novel characterization process of rosacea by identifying for the first time in the inflammatory process the involvement of Th17 cells as well as the therapeutic applications targeting the functions of the Th17 cells in rosacea.

More specifically, the invention proposes the use of ROR gamma t (also known as RAR-related orphan receptor C or retinoic acid-related orphan receptor (ROR)[gamma]t or ROR C variant 2 or RORγ2)), or ROR alpha (also called RORA or RAR-related orphan receptor A), and their use to diagnose rosacea and/or to screen inhibitors of Th17 differentiation, notably in inhibiting ROR gamma t or ROR alpha and the use of these screened inhibitors in rosacea treatment.

Rosacea is commonly described as a chronic and progressive inflammatory dermatosis related to vascular relaxation. The inflammatory process is characterized by a vascular response to physical and pathogen aggression. In the case of rosacea, this physical response manifests itself by redness of the central part of the face or hot flushes, facial erythema, papules, inflammatory pustules, telangiectasia and sometimes ocular lesions called ocular rosacea. In serious cases, particularly in men, the soft tissue of the nose may swell and produce a bulbous swelling known as rhinophyma. The result of this facial vascular abnormality is a permanent oedema of the dermis, which may be accompanied by an increased colonization by the parasite *Demodex folliculorum* present on the skin of patients.

Rosacea generally occurs between the ages of 25 and 70, and it is much more common in people with a light complexion. It affects more particularly women, although this condition is generally more serious in men. Rosacea is chronic and persists for years with periods of exacerbation and remission.

According to the National Rosacea Society, rosacea can be classified into four subtypes plus one variant known as granulomatous rosacea. These subtypes are taken up below:

First Subtype—Erythematotelangiectatic Rosacea:

It is mainly characterized by episodic erythema and persistent central facial erythema. The appearance of telangiectasia is customary but not essential for a diagnosis of this first subtype. Central facial oedema, burning sensations and squamae are also symptoms that have been reported. Conventionally, patients experience erythrosis attacks due to the abrupt dilation of the arterioles of the face, which then takes on a congestive, red appearance. These attacks can in particular be brought on by emotions, meals and changes in temperature.

Second Subtype—Papulopustular Rosacea:

It is characterized by a persistent central facial erythema with the appearance of central facial papules or pustules. However, the papules and the pustules can also occur in the periorificial regions, i.e. in the perioral, perinasal, or periocular regions. This second subtype resembles common rosacea, except for the fact that the comedones are absent. Burning sensations may also appear. This subtype has often been seen after or in combination with the first subtype. Telangiectasias are often observed after or with the first rosacea subtype. These telangiectasias may be obscured by the erythema, the papules, or the persistent pustules. Some patients also exhibit oedema on the cheeks and the forehead.

Third Subtype—Phymatous Rosacea

This subtype is characterized by a thickening of the skin and irregular surface nodularities. Rhinophyma most commonly appears, but phymatous rosacea can also appear in other areas such as the chin, the forehead, the cheeks and the ears. Patients suffering from this subtype may also exhibit enlarged and prominent opening of the follicles. This subtype is also often observed after or in combination with subtype 1 or 2, including erythema, telangiectasias, papules and persistent pustules. In the case of rhinophyma, these additional stigmata may be particularly pronounced in the nasal region.

Fourth Subtype—Ocular Rosacea

The diagnosis of rosacea should be considered when the eyes of a patient show one or more of the following signs and symptoms: bloodshot appearance of the conjunctiva, excessive watering, feeling of a foreign body in the eye, burning, dryness, pruritus, photophobia, blurred vision, conjunctival telangiectasias or eyelid margin telangiectasias, periocular erythema, blepharitis, conjunctivitis, and Meibomius gland dysfunction. These signs or symptoms occur before, during or after the appearance of the cutaneous signs. Ocular rosacea is most commonly diagnosed when other cutaneous symptoms are present. However, the cutaneous signs are not necessary for the diagnosis, and studies suggest that the ocular signs and symptoms can occur, in 20% of cases, before the cutaneous manifestations.

Granulomatous Variant:

There is also a granulomatous variant of rosacea which is characterized by hardened yellow, brown or red papules or nodules, and also monomorphic lesions at the site of the papules. Other signs of rosacea may also be present.

Of course, the pathological manifestations of rosacea vary according to the subtype of the disease. However, it will be noted that patients may have characteristics of several different subtypes at the same time. It will also be noted that the disease does not necessarily progress from one subtype to the other (Wilkin et al., 2002, J. AM. Acad. Dermatol. Vol. 46, pages 584-587).

Many aggression factors may be involved without necessarily inducing this condition. They are, for example, psychological factors, gastrointestinal disorders, environmental factors (exposure to sunlight, temperature, humidity), emotional factors (stress), dietary factors (alcohol, spices), hormonal factors, vascular factors, or even infection with pathogen *Helicobacter pilori*.)

Moreover, it has been demonstrated that in Rosacea, neutrophils play an important role not only in the development of inflammatory lesions but also of erythema and telangiectasia (Millikan L. The proposed inflammatory pathophysiology of *Rosacea: implications for treatment. Skinmed* 2003; 2: 43-47).

Thus, inflammatory events are a key cause of rosacea.

In this context, for the first time, the applicant proposes with experimental evidences to target a novel inflammatory process, TH17 differentiation, for treating and diagnosing rosacea.

Thus, the invention is relating to the use of the DNA or the mRNA encoding ROR gamma t, and also the corresponding proteins, as markers for rosacea as well as the use of the DNA or the mRNA encoding ROR alpha and also the corresponding proteins, as markers for rosacea. The invention is also relating to the use of at least one of the proposed above proposed markers and/or at least one of the markers chosen from IL-6, IL-17A, IL-17F, IL-21, IL-22, IL-26, TNF alpha and CCL20, as markers for rosacea.

The invention also provides a method for the diagnosis of rosacea, comprising the following steps:
a) detecting the level of expression of at least one of the proposed markers of the invention (ROR gamma t or ROR alpha) and/or at least one of the markers chosen from IL 6, IL-17A, IL-17F, IL-22 and CCL20 in a sample taken from an individual,
b) detecting the level of expression of at least one of the proposed markers and/or at least one of the markers chosen from IL-6, IL-17A, IL-17F, IL-22 and CCL20 in a sample taken from a healthy individual,
c) comparing the difference in level of expression of at least one marker and for which the level of expression is significantly higher than the level of expression in the healthy individual;
d) the overexpression of at least one of the markers of step c) being an indicator of rosacea, thus diagnosing rosacea.

The invention provides also a method for the diagnosis of rosacea that can also comprise the following steps:
a) detecting the level of expression of at least one of the proposed markers in a sample taken from an individual,
b) detecting the level of expression of at least one of the proposed markers in a sample taken from a normal individual,
c) comparing the difference in level of expression of at least one marker and for which the level of expression is significantly higher than the level of expression in the healthy individual;
d) the overexpression of at least one of the markers of step c) being an indicator of rosacea, thus diagnosing rosacea.

The invention provides a method for monitoring the progression or variation of rosacea, comprising the following steps:
 a) taking a biological sample from the individual,
 b) analysing the level of expression of at least one of the proposed markers, and/or at least one of the markers chosen from IL-6, IL-17A, IL-17F, IL-22 and CCL20 in a sample taken and in which a variation in the expression of at least one of the markers is an indicator of the progression of rosacea.

Progression of rosacea may be from a predominantly vascular to a more inflammatory dominated state, it may also mean progression towards specific rosacea subtypes as described above. Progression might also occur in the other direction, from a more severe to a less severe form of rosacea.

The invention provides also a method for monitoring the efficacy of a treatment intended for treating rosacea, comprising the following steps:
 a) administering the desired treatment to the individual identified as having one or more of the symptoms of rosacea,
 b) taking a biological sample from the individual,
 c) analysing the level of expression of at least one of the proposed markers and/or at least one of the other markers chosen from 11-6, IL-17A, IL-17F, IL-22 and CCL20, in which a variation in the expression of at least one of the markers is an indicator of efficacy in the treatment of rosacea.

The invention provides also a in vitro screening method of Th17 cell differentiation inhibitors, comprising determining the capacity of said candidate to inhibit or down regulate expression and/or the biological function of one of the proposed markers.

More specifically, the invention relates to an in vitro screening method of Th17 cell differentiation inhibitors for the identification of drug candidates, comprising the following steps:
a) Collecting at least two biological samples: one mimics the rosacea lesion, and one mimics the healthy condition;
b) Contacting at least one sample or a mixture of samples with one or more drug candidates to be tested;
c) Detecting the expression or biological function of at least one of the proposed markers, and/or at least one of the expression markers selected from: IL-6, IL-17A, IL-17F, IL-22 and CCL20 in the biological samples or mixture obtained in b);
d) Selecting drug candidates which are capable of inhibiting the expression or biological function of at least one of the proposed markers, and/or the expression of at least one of the expression markers selected from IL-6, IL-17A, IL-17F, IL-22 and CCL20 measured in said samples or mixtures obtained in b) and comparing the levels with a sample not mixed with the drug candidate (s).

In another embodiment, the invention provides an in vitro screening method of Th17 cell inhibitors for drug candidate identification, comprising the following steps:
a) Collecting at least two biological samples: one mimics the rosacea lesion, and one mimics the healthy condition;
b) Contacting at least one sample or a mixture of samples with one or more drug candidates to be tested;
c) Detecting the expression or biological function of at least one of the proposed markers in the biological samples or mixture obtained in step b);
d) Selecting drug candidates which are capable of inhibiting the expression or biological function of at least one marker chosen from the proposed markers measured in said samples or mixture obtained in step b) and comparing the levels or biological function with a sample not mixed with the drug candidate.

The invention relates also to the use of inhibitors identified by screening methods as defined above for the preparation of a composition for treating rosacea and/or rosacea associated disorders. More specifically, the invention encompasses the use of inhibitors of the proposed markers identified by screening methods for the preparation of a composition for treating rosacea or rosacea associated disorders such as N-(2,2,2-trifluoroethyl)-N-[4-[2,2,2-trifluoro-1-hydroxy-1-(trifluoromethyl)ethyl]phenyl]-benzenesulfonamide, 2 oxysterol (oxygenated sterols), especially 24S-hydroxycholesterol 24(S), 25-epoxycholesterol and 7-oxygenated sterols, Methyl 2-cyano-3,12-dioxooleana-1, 9(11)dien-28-oate or Bardoxolone methyl, -(8S,9R,10R, 13R,14S,16R,17R)-17-[(E,2R)-2,6-dihydroxy-6-methyl-3-oxohept-4-en-2-yl]-2,16-dihydroxy-4,4,9,13,14-pentamethyl-8,10,12,15,16,17-hexahydro-7H-cyclopenta[a]phenanthrene-3,11-dione, 5-(4-chlorophenyl)-6-ethylpyrimidine-2,4-diamine, gamma-D-glutamyl-L-tryptophan, 8-hydroxy-3-methyl-3,4-dihydro-2H-benzo[a]anthracene-1,7,12-trione, 5,7-dihydroxy-2-(4-hydroxyphenyl)-4-oxo-4H-chromen-3-olate, methyl-N-[4-(trifluoromethyl)phenyl]-1,2-oxazole-4-carboxamide or Leflunomide, N—[(E)-(3-methylphenyl)methylideneamino]-6-morpholin-4-yl-2-(2-pyridin-2-ylethoxy)pyrimidin-4-amine.

BRIEF DESCRIPTION OF THE DRAWINGS

FIG. 1 provides mRNA expression levels of specific cytokines characterizing Th17 cells in lesional skin.

FIG. 2 shows the protein expression levels of specific cytokines in in rosacea lesional skin.

DETAILED DESCRIPTION

Indeed, Th17 cells, a distinct Th lineage originating from the differentiation of naïve CD4+ T cells, provide immunity against a variety of extracellular pathogens, including bacteria and fungi. Moreover, Th17 cells have also been implicated in a variety of inflammatory and autoimmune disorders, such as psoriasis, rheumatoid arthritis and multiple sclerosis (Peck A, Mellins E D. Precarious balance: Th17 cells in host defense. Infect Immun. 2010 January; 78(1): 32-8).

At the molecular level, Th17 cells are characterized by the production of a distinct profile of effector cytokines, IL-17A, IL-17F, IL-26, IL-22, IL-21 and TNFα and depend upon IL-23 for their development, survival and proliferation. These cytokines activate different types of cells, such as keratinocytes, leading to their hyperproliferation and further production of proinflammatory cytokines, chemokines and antimicrobial peptides, which in turn recruit and activate other immune cells in the inflamed skin, leading to amplification of the inflammatory response. Moreover, IL-17A, and IL-17F leading to an autocrine regulation of IL-17 production which serves to promote and sustain Th17 cell differentiation (Wei et al. 2007, J. Biol. Chem., September 20). 11-17 is also responsible for the upregulation of CCL20, the ligand of a characterized receptor of the TH17 cells in stromal cells, allowing the attraction of additional Th17 cells into inflamed tissue.

This differentiation phenotype characterized with the effector cytokines quoted above is the result of a signalling pathway which requires extracellular molecules such as TGFb-1, implicated in the naive CD4 T cell differentiation into Th17 cells, either in combination with IL-21, with IL-1b and IL-23 or with IL-1b, IL-23, and IL-6 (Chung Y et al. Critical regulation of early Th17 cell differentiation by interleukin-1 signaling. Immunity 2009; 30:576-87, Veldhoen M, Hocking R J, Atkins C J, Locksley R M, Stockinger B. Immunity. 2006 February; 24(2):179-89) and lead to the expression of retinoid-related orphan receptor (RORC) and retinoid-related orphan receptor alpha (RORA), which promote TH17 differentiation and substantially upregulate IL-17A and IL-17F expression.

The signalling pathways of the naive CD4 T cell differentiation into Th17 cells required TGFb-1 either in combination with IL-21, with IL-1b and IL-23 or with IL-1b, IL-23, and IL-6 (Chung Y et al. Critical regulation of early Th17 cell differentiation by interleukin-1 signalling. Immunity 2009; 30:576-87, Veldhoen M, Hocking R J, Atkins C J, Locksley R M, Stockinger B. and Immunity. 2006 February; 24(2):179-89).) and lead to the expression of retinoid-related orphan receptor (RORC) and retinoid acid-related orphan receptor alpha (RORA), which are two genes that promote TH17 differentiation and substantially upregulate IL-17A and IL-17F expression.

For the following, "Th17 differentiation profile molecules" refers to the biological molecules that characterize the TH17 differentiation that is to say the cytokines and factors on whom depends the differentiation from naïve T cells (11-6, Il-26, IL-23 A), the effector cytokines produced by TH17 cells (IL-17 A, IL-17F, IL-21, IL-22, IL-26, TNF alpha and CCL20), or receptors expressed by TH17 cells (CCR6, IL23R).

Animal experiments place mROR-γt (the mouse ortholog of human ROR gamma t) in the rank of a master regulator of Th-17 differentiation. ROR gamma t deficiency in mice results in diminished Th17 activity and severely reduced expression of IL-17 (Ivanov I I, McKenzie B S, Zhou L, Tadokoro C E, Lepelley A, Lafulle J J, Cua D J, Littman D R. The orphan nuclear receptor ROR gamma t directs the differentiation program of proinflammatory IL-17+T helper cells. Cell. 2006 Sep. 22; 126(6):1121-33).

Therefore, the invention provides the ROR gamma t or ROR alpha, crucial actors of TH17 cell differentiation as novel markers for characterizing rosacea with the examples which follow.

In particular embodiment, the invention provides the use of the DNA or the mRNA encoding ROR gamma t and also the corresponding proteins, as markers for rosacea.

In particular embodiment, the invention provides the use of the DNA or the mRNA encoding ROR alpha and also the corresponding proteins, as markers for rosacea.

In another embodiment, the invention provides the use of at least one of the proposed markers with at least one of the markers chosen from IL-6, IL-17A, IL-17F, 11-21, IL-22, Il-23A, IL-26 and CCL20, as markers for rosacea.

In another embodiment, the invention provides the use of at least one of the proposed markers and/or at least one of the markers selected from the following list: IL-6, IL-17 A, IL-17F, IL-22, CCL20, as markers for rosacea.

For the purpose of the present invention, the term "marker" or "biological marker" denotes a biological marker associated with the presence or with the absence of a particular pathological state. The biological markers are in particular proteins, mRNAs or DNAs.

For more clarity, the following definitions are used: The term "Proposed markers" means ROR gamma t and/or ROR alpha. "ROR gamma t", means either the expression product of RORC variant 2, i.e ROR gamma mRNA or protein or the RORC gene itself. In analogy, "ROR alpha" means either the expression product of the RORA gene, i.e ROR alpha mRNA or protein or the RORA gene itself.

The term "level of expression" or "expression" means the level of mRNAs or proteins encoded by the gene marker.

The expression level analysis or detection can be performed by any suitable method, known to those skilled in the art, such as western blotting, 1HC, mass spectrometry (Maldi-TOF and LC/MS analyses), radioimmunoassay (RIA), Elisa or any other method known to those skilled in the art or else by assaying the mRNA according to the methods customarily known to those skilled in the art. The techniques based on the hybridization of mRNA with specific nucleotide probes are the most customary (Northern blotting, RT-PCR (Reverse Transcriptase Polymerase Chain Reaction), quantitative RT-PCR (qRT-PCR), RNase protection).

In one embodiment, the invention relates to a method for the diagnosis of rosacea, comprising the following steps:
 a) detecting the level of expression of at least one of the proposed above markers, and/or at least one of the markers chosen from IL-17A, IL-17F, IL-22, IL-26 and CCL20 in a sample taken from an individual,
 b) detecting the level of expression of and at least one of the above markers, and at least one of the markers chosen from IL-17A, IL-17F, IL-22, IL-26 and CCL20 in a sample taken from a normal individual,
 c) comparing the difference in level of expression of at least one marker and for which the level of expression is significantly higher than the level of expression in the healthy individual;

d) the overexpression of at least one of the markers of step c) being an indicator of rosacea, thus diagnosing rosacea.

The method for the diagnosis of rosacea can also comprise the following steps:
a) detecting the level of expression of at least one of the proposed markers in a sample taken from an individual,
b) detecting the level of expression of at least one of the proposed markers in a sample taken from a normal individual,
c) comparing the difference in level of expression of at least one marker and for which the level of expression is significantly higher than the level of expression in the healthy individual;
d) the overexpression of at least one of the markers of step c) being an indicator of rosacea, thus diagnosing rosacea.

In particular, the described diagnostic methods can be applied for the diagnostic of subtype 2 with the overexpression of the following markers: I-L26, CCL20, IL-22, IL-17A, IL-6, and TNF alpha.

In particular, the described diagnostic methods can be applied for the diagnostic of subtype 2 and 3 with the overexpression of the following proposed markers: IL-26, CCL20.

According to another aspect the invention is related to a method for monitoring the progression or variation of rosacea, comprising the following steps:
a) taking a biological sample from the individual,
b) analysing the level of expression of at least one of the proposed markers, and at least one of the markers chosen from IL-6, IL-17A, IL-17F, IL-22, IL-26 and TNF alpha, CCL20 in a sample taken and in which a variation in the expression of at least one of the markers is an indicator of the progression of rosacea.

Thus, the invention relates also to a method for the prognosis of the progression or variation of rosacea.

According to another aspect the invention is related to a method for monitoring the efficacy of a treatment intended for treating rosacea, comprising the following steps:
a) administering the desired treatment to the individual identified as having one or more of the symptoms of rosacea,
b) taking a biological sample from the individual,
c) analysing the level of expression of at least one of the proposed markers with at least one of the other markers chosen from IL-6, IL-17A, IL-17F, IL-22, IL-26 and TNF alpha, CCL20, in which a variation in the expression of at least one of the markers is an indicator in the treatment of rosacea.

The expression "overexpression of one of the factors or markers" is intended to mean a level of expression increased by at least 50%, and preferably by at least 100%, and even more preferably by at least 200%, or expressed differently with equivalent significance, by at least a factor of 2, or at least twice as high as the level in a normal individual; which demonstrates overall an overexpression of the chemokines, the cytokines and the receptors mentioned above, thus representing markers characteristic of rosacea.

In the context of the invention, the biological sample corresponds to any type of sample taken from an individual, and can be a tissue sample or a fluid sample, such as blood, lymph or interstitial fluid.

According to one particular and preferred embodiment, the sample is a biopsy of varying size (preferably from 1 to 6 mm in diameter), or a skin sample taken by means of tape stripping, such as with D-Squames, according to the method described in Wong R et al., "Analysis of RNA recovery and gene expression in the epidermis using non-invasive tape stripping"; J Dermatol Sci.2006 November; 44(2):81-92; or in Benson N R, et al., "An analysis of select pathogenic messages in lesional and non-lesional psoriatic skin using non-invasive tape harvesting". J Invest Dermatol. 2006 October; 126(10): 2234-41; or else in Wong R et al., "Use of RT-PCR and DNA microarrays to characterize RNA recovered by non-invasive tape harvesting of normal and inflamed skin". J Invest Dermatol. 2004 July; 123(1):159-67. According to the principle of tape stripping, the product used comprises a flexible translucent polymer support and an adhesive. The product is applied repeatedly to the skin of the patient, preferably until loss of adhesion. The sample obtained relates only to the content of the outermost layers of the epidermis. A method for analysing a protein content obtained in particular according to this sampling method is described in Patent Application WO2009/068825 (Galderma R&D) in order to monitor markers specific for a pathological skin condition and to orient the diagnosis. Since this method is rapid, non-invasive and relatively inexpensive for detecting the presence of, the absence of or the variation in certain proteomic markers, it is particularly preferred. This method is in particular characterized by mass spectrometry detection, ELISA or any other method known to the expert skilled in the art of protein quantification. Quantification is performed in the skin sample obtained on the flexible and adhesive support in order to detect at least one protein of which the presence, the absence or the variation in amount or in concentration compared with a standard value is associated with the presence, with the progression or with the absence of a particular pathological skin condition.

Another embodiment of the present invention is an in vitro screening method of Th17 cell differentiation candidate inhibitors, comprising determining the capacity of said candidate to inhibit and/or down regulate the expression or the biological activity or the biological function, including the transactivation properties, of at least one of the proposed markers (RORgamma t or RORalpha) of the invention.

The identified candidate will influence the biological function of a given marker or a biological process modulated by the marker. For example, the inhibition of ROR gamma t and/or ROR alpha by a candidate may affect the biological function of ROR gamma t, including the induction of the Th17 cell differentiation as well as the function of Th17 cells.

Another embodiment of the present invention is in vitro screening method of TH17 differentiation inhibitors, comprising determining the capacity of said candidate to inhibit or down regulate expression one of the proposed markers.

For the screening, biological samples are transfected cells containing reporter gene operably under the control of a promoter (totally or partially) controlling the expression of an above mentioned gene. Therefore step c) above consists to measure the expression of the reporter gene.

The reporter gene may encode an enzyme that with its corresponding substrate, provides coloured product(s) such as CAT (chloramphenicol acetyltransferase), GAL (beta galactosidase), or GUS (beta glucuronidase). It might be either luciferase or GFP (Green Fluorescent Protein) gene. Reporter gene protein dosage or its activity is typically assessed by colouring, fluorometric or chemoluminescence methods.

According to a second embodiment of the invention, biological samples are cells expressing the gene of interest and the step c) above consists to measure the activity of the gene product.

Any kind of cell is suitable for the invention. Cells may endogenously express the said gene like lymphocytes. Organs may be suitable for the instant invention, from animal or human origin like lymph nodes.

Transformed cells by heterologous nucleic acid encoding the gene expression product of interest might be suitable. Preferably the said nucleic acid is from animal (preferred mammal) or human origin. A large variety of host cells is suitable for the invention and in particular Cos-7, CHO, BHK, 3T3, HEK293 cells. Cells are transiently or permanently transfected by a nucleic acid of interest with a well known by skilled in the art method and for instance calcium phosphate precipitation, DEAE-dextran, liposome, virus, electroporation or microinjection.

The gene expression of step c) is determined with the same techniques quoted above for diagnostic.

The compounds to be tested are any kind of compounds, from natural or synthetic source. As synthetic compounds they might be chemically synthesized or from chemical compound data bank, with a defined structure or non characterized or present in a mixture of compounds.

Several technical assays are available for assessing compounds activity modulating above mentioned biomarkers/gene expression products.

In other embodiment, the invention is related to the use of identified inhibitors with the described screening methodes for the preparation of a composition for treating rosacea or rosacea associated disorders.

According to another aspect the invention is related to a method for monitoring the progression or variation of rosacea, comprising the following steps:
a) taking a biological sample from the individual,
b) analysing the level of expression of at least one of the proposed markers, and at least one of the markers chosen from IL-17A, IL-22, IL-26, TNF alpha and CCL20 in a sample taken and in which a variation in the expression of at least one of the markers is an indicator of the progression of rosacea.

According to another aspect the invention is related to a method for monitoring the efficacy of a treatment intended for treating rosacea, comprising the following steps:
a) administering the desired treatment to the individual identified as having one or more of the symptoms of rosacea,
b) taking a biological sample from the individual,
c) analysing the level of expression of at least one of the proposed markers with at least one of the other markers chosen from IL-17A, IL-22, IL-26, TNF alpha and CCL20, in which a variation in the expression of at least one of the markers is an indicator in the treatment of rosacea.

Another embodiment of the present invention is in vitro screening method of TH17 differentiation inhibitors, comprising determining the capacity of said candidate to inhibit or down regulate expression one of the proposed markers.

In one aspect, the In vitro screening method of TH17 differentiation inhibitor for drug candidate, comprise the following steps:
a) Collecting at least two biological samples: one mimics the rosacea lesion, and one mimics the healthy condition;
b) Contacting at least one sample or a mixture of samples with one or more drug candidates to be tested;
c) Detecting the expression of at least one of the proposed markers, and at least one of the expression markers chosen from: IL-17A, IL-22, IL-26, TNF alpha and CCL20 in the biological samples or mixture obtained in b);
d) Selecting drug candidates which are capable of inhibiting the expression of IL-17A, IL-22, IL-26, TNF alpha and CCL20 measured in said samples or mixtures obtained in b and comparing the levels with a sample not mixed with the drug candidate.

The reporter gene may encode an enzyme that with its corresponding substrate, provides coloured product(s) such as CAT (chloramphenicol acetyltransferase), GAL (beta galactosidase), or GUS (beta glucuronidase). It might be either luciferase or GFP (Green Fluorescent Protein) gene. Reporter gene protein dosage or its activity is typically assessed by colouring, fluorometric or chemoluminescence methods.

According to a second embodiment of the invention, biological samples are cells expressing the gene of interest and the step c) above consists to measure the activity of the gene product.

Any kind of cell is suitable for the invention. Cells may endogenously express the said gene like lymphocytes. Organs may be suitable for the instant invention, from animal or human origin like lymph nodes.

Transformed cells by heterologous nucleic acid encoding the gene expression product of interest might either be suitable. Preferably the said nucleic acid is from animal (preferred mammal) or human origin. A large variety of host cells is suitable for the invention and in particular Cos-7, CHO, BHK, 3T3, HEK293 cells. Cells are transiently or permanently transfected by a nucleic acid of interest with a well known by skilled in the art method and for instance calcium phosphate precipitation, DEAE-dextran, liposome, virus, electroporation or microinjection.

The gene expression of step c) is determined with the same techniques quoted above for diagnostic.

The compounds to be tested are any kind of compounds, from natural or synthetic source. As synthetic compounds they might be chemically synthesized or from chemical compound data bank, with a defined structure or non characterized or present in a mixture of compounds.

Several technical assays are available for assessing compounds activity modulating above mentioned biomarkers/gene expression products.

According to a further embodiment of the invention, biological samples are cells expressing the gene of interest and the step c) above consists to measure the activity of the gene product.

In another embodiment, the invention is related to the use of identified inhibitors/antagonists/inverse agonists with the described screening methods for the preparation of a composition for treating rosacea and/or rosacea associated disorders.

In particular, the inhibitors/antagonists/inverse agonists of gamma t or ROR alpha could be selected from the following list: —N-(2,2,2-trifluoroethyl)-N-[4-[2,2,2-trifluoro-1-hydroxy-1-(trifluoromethyl)ethyl]phenyl]-benzenesulfonamide; this compound is a novel retinoic acid receptor-related orphan receptor-alpha/gamma inverse agonist. (Mol. Pharmacol. 2010 February; 77(2):228-36))

2 oxysterol (oxygenated sterols), especially 24S-hydroxycholesterol 24(S),25-epoxycholesterol and 7-oxygenated sterols [a second class of nuclear receptors for oxysterols: Regulation of RORalpha and RORgamma activity by 24S-hydroxycholesterol (cerebrosterol)- Wang Y et al. Biochim Biophys Acta. 2010 August; 1801(8):917-23. Epub 2010 Mar. 6]; Wang Y et al. Modulation of retinoic acid receptor-related orphan receptor alpha and gamma activity by 7-oxygenated sterol ligands. J Biol. Chem. 2010 Feb. 12; 285(7): 5013-25))

Methyl2-cyano-3,12-dioxooleana-1,9(11)dien-28-oate or Bardoxolone methyl (also known as "RTA 402" and "CDDO-methyl ester").

(8S,9R,10R,13R,14S,16R,17R)-17-[(E,2R)-2,6-dihydroxy-6-methyl-3-oxohept-4-en-2-yl]-2,16-dihydroxy-4,4,9,13,14-pentamethyl-8,10,12,15,16,17-hexahydro-7H-cyclopenta[a]phenanthrene-3,11-dione or SI-124 (Blaskovich M A, Sun J, Cantor A et al. Discovery of JS-124 (cucurbitacin I), a selective Janus Kinase/Signal Transducer and Activator of Transcription 2 signaling pathway inhibitor with potent antitumor activity against human and murine cancer cells in mice Cancer Res 2003; 63: 1270-1279)

Pyrimethamine: -5-(4-chlorophenyl)-6-ethylpyrimidine-2,4-diamine or Pyrimethamine (Dariprim)(WO/2008/156644)

gamma-D-glutamyl-L-tryptophan or SCV-07 (SciClone Pharmaceuticals)(Nagabhushanam V, Subbarao K, Ramachandran M et al Inhibition of STAT3 driven gene expression in melanoma cells by SCV-07 J Clin Oncol 2008; 26 (May 20, suppl): 14619)

8-hydroxy-3-methyl-3,4-dihydro-2H-benzo[a]anthracene-1,7,12-trione or STA-21 (Song H, Wang R, Wang S et al. A low-molecular-weight compound discovered through virtual database screening inhibits Stat3 function in breast cancer cells PNAS 2005; 102: 4700-4705 natural flavonol: such as 5,7-dihydroxy-2-(4-hydroxyphenyl)-4-oxo-4H-chromen-3-olate or Kaempferol (Bruno R D, Njar V C. Targeting cytochrome P450 enzymes: a new approach in anti-cancer drug development. Bioorg Med. Chem. 2007 Aug. 1; 15(15):5047-60. Epub 2007 May 23).

methyl-N-[4-(trifluoromethyl)phenyl]-1,2-oxazole-4-carboxamide or Leflunomide (O'Donnell E F, Saili K S, Koch D C, Kopparapu P R, Farrer D, Bisson W H, Mathew L K, Sengupta S, Kerkyliet N I, Tanguay R L, Kolluri S K. The anti-inflammatory drug leflunomide is an agonist of the aryl hydrocarbon receptor. PLoS One. 2010 Oct. 1; 5(10).

N—[(E)-(3-methylphenyl)methylideneamino]-6-morpholin-4-yl-2-(2-pyridin-2-ylethoxy)pyrimidin-4-amine or STA 5326 (Apilimod Synta pharmaceuticals) Wada et al: Selective abrogation of Th1 response by STA-5326, a potent IL-12/IL-23 inhibitor. Blood, 2007, 109(3), 1156-1164.; Wada et al: IL-12/IL-23 inhibitors: a promising approach to the treatment of inflammatory disorders. Drugs Fut. 2008, 33(1), 49-63-[(3S,5R,8R, 9S,10S,12R,13S,14S)-3-[(2S,4S,5R,6R)-5-[(2S,4S,5R, 6R)-5-[(2S,4S,5R,6R)-4,5-dihydroxy-6-methyl-oxan-2-yl]oxy-4-hydroxy-6-methyl-oxan-2-yl]oxy-4-hydroxy-6-methyl-oxan-2-yl]oxy-12,14-dihydroxy-10, 13-dimethyl-1,2,3,4,5,6,7,8,9,11,12,15,16,17-tetra decahydrocyclopenta[a]phenanthren-17-yl]-5H-furan-2-one or Digoxin and its derivatives.

In other aspect, inhibitors might be either a polypeptide, a DNA or RNA antisens, a si-RNA or a PNA (Peptide nucleic acid), i-e with a polypeptidic chain substituted by purine and pyrimidine bases and having a DNA-like structure for hybridization to this latter)

The modulator might be an antibody and preferably a monoclonal antibody. Advantageously, the monoclonal antibody is administered to a patient in a sufficient quantity so as the measure a plasmatic concentration from about 0.01 µg/ml to about 100 µg/ml, preferred from about 1 µg/ml to about 5 µg/ml.

The invention is intended for treating Rosacea® By rosacea it is understood, all rosacea subtypes as well as rosacea associated disorders.

The example which follows illustrates the invention without limiting the scope thereof.

Table 1: mRNA expression measured by Affymetrix of the expression of TH17 differentiation profile molecules: IL-17A, IL-26, IL-22, TNF alpha, CCL20, IL-6 and proposed markers: RORC and RORA as well as IL5, IL4 IL13 typically considered as Th2 cytokines.

Table 2: Expression of cytokines released by T-helper cells (Luminex assay). Analysis of IL-22, CCL20, IL-17F, characteristic of Th17 cells, as well as IL-5, IL-4 and IL-13 typically considered as Th2 cytokines Example 1: Modulation of the TH17 Molecular Profile in the Lesional Skin of Patients Suffering from Rosacea Compared with Non Lesional Skin of these Patients: Analysis of the Expression of IL-6, IL-17 A, IL-22, IL-26, TNF Alpha, CCL20 and the Proposed Markers RORA and RORC Patient Selection and Tissue Biopsie:

Skin biopsies of rosacea patients with rosacea subtype I (n=11), II (n=11) and III (n=6) were performed, in accordance with good clinical practice. (The clinical description of rosacea subtypes was carried out according to the classification of Wilkin et al., 2002, J. Am. Acad. Dermatol. Vol 46, pages 584-587.)

To evaluate a change in the expression level of the genes, the expression levels in lesional skin are compared with the expression levels in non-lesional skin of the same subjects (n=12).

mRNA extraction, labelling and hybridization to probe arrays: The mRNA was isolated from skin using the RNeasy extraction kit (Quigen Inc., Valencia, Calif.) and quality was evaluated using a 2100 Bioanalyser of Agilent. The mRNA expression was evaluated by a Gene Chip IVT labelling kit after the generation of double-stranded cDNA (i.e in vitro transcription process) using T7-oligo primer and the one cycle cDNA synthesis kit of Affymetrix. RNA was ethanol precipitated to concentrate the sample and then quantified using a spectrophotometer. Approximately 200 ng of total RNA of good quality [RNA indication number (RIN) 7] from each sample was used to generate double-stranded cDNA using a T7-oligo (dt) primer (one cycle cDNA synthesis kit, Affymetrix). Biotinylated cRNA, produced through in vitro transcription (Gene Chip IVT labelling kit, Affymetrix) was fragmented and hybridised to an Affymetrix human U133A 2.0 plus microarray. The arrays were processed on a Gene Chip Fluidics Station 450 and scanned on an Affymetrix Gene Chip Scanner (Santa Clara, Calif.).

Statistical Analysis of mRNA Expression:

The expression data from Affymetrix Gene Chips are normalized with RMA (Robust Multi-array Analysis) method. The raw intensity values are background corrected, log 2 transformed and then quantile normalized. Next a linear model is fit to the normalized data to obtain an expression measure for each probe set on each array. To identify genes that were significantly modulated in the different Rosacea subtype samples, one-way ANOVA with Benjamini-Hochberg multiplicity correction was performed using JMP 7.0.1 (SAS Institute) and irMF 3.5 (National Institute of Statistical Sciences, NISS) software.

The table 1 shows the mRNA of specific cytokines characterizing Th17 cells, IL-17A, IL-26, TNF alpha, CCL20 are significantly up-regulated in lesional skin (table 1). Thus, inhibiting or targeting TH17 differentiation process have a proved interest for or treating or diagnosing rosacea. Moreover, in these tables, the mRNA expression of IL-5, IL-4 and IL-13 are not detected or not changed suggesting that the inflammatory response in all Rosacea subtypes is not driven by Th2 cells.

The mRNA levels of transcription factors including RORC and RORA are not modulated in rosacea, but their expression in human skin was clearly demonstrate. Thus they are interesting markers for diagnosing rosacea, screening inhibitors of TH17 differentiation in using them alone or combined or with at least one of Th17 differentiation profile molecules, screening inhibitors of TH17 differentiation.

Example 2: Cytokine Extraction and Assay

Proteins were extracted from skin biopsies in healthy volunteers and from lesional skin in patients with rosacea (subtype I or II). Cytokines were dosed in the protein extracts using Luminex assays (Millipore & Procarta cytokine dosage kits). The cytokine quantities were normalized to the total concentration of protein. Paired P-values were calculated for each cytokine.

Table 2 shows a significant up-regulation of the protein expression level of IL-22, CCL20, IL-17F in rosacea lesional skin (type I and II) in comparison to healthy skin, indicating a Th17-driven response. Like at the mRNA levels, IL-5, IL-4 and IL-13 are not significantly modulated in rosacea lesional skin, indicating the absence of a Th2-driven response.

The invention claimed is:

1. A method of detecting a level of gene expression of a marker for rosacea subtype I, subtype II, or subtype III in a patient, the method comprising:
   (a) obtaining a skin sample from a patient suspected of having rosacea subtype I, subtype II, or subtype III;
   (b) measuring gene expression of IL 26, and/or CCL20 in the skin sample;
   (c) comparing the gene expression of IL 26, and/or CCL20 in the skin sample against a level of gene expression of IL 26, and/or CCL20 in a control skin sample of a healthy individual.

2. A method for monitoring efficacy of a treatment intended for treating rosacea subtype I, subtype II, or subtype III, the method comprising:
   (a) administering a desired treatment to an individual identified as having one or more symptoms of rosacea subtype I, subtype II, or subtype III,
   (b) taking skin samples from the individual before, during, and/or after the administration,
   (c) comparing gene expression of IL-26, and/or CCL20, in the skin samples.

3. The method of claim 1, wherein the skin sample is from a biopsy.

4. The method of claim 1, wherein the skin sample from the patient is from a patient suspected of having rosacea subtype I or subtype II.

5. The method of claim 1, wherein the expression in the patient is at least 50% more than the expression in the control sample.

6. The method of claim 5, wherein the expression in the patient is at least 100% more than the expression in the control sample.

7. The method of claim 5, wherein the expression in the patient is at least 200% more than the expression in the control sample.

8. The method of claim 1, wherein (b) further comprises measuring gene expression of IL-6, IL-17A, IL-17F, IL-22, and/or TNF alpha, in the skin sample; and (c) further comprising comparing the gene expression of IL-6, IL-17A, IL-17F, IL-22, and/or TNF alpha, in the skin sample against a level of expression of IL-6, IL-17A, IL-17F, IL-22, and/or TNF alpha in a control skin sample of a healthy individual.

9. The method of claim 8, wherein the skin sample from the patient is from a patient suspected of having rosacea subtype II.

10. The method of claim 1, wherein (b) further comprises measuring gene expression of IL-17A in the skin sample; and (c) further comprising comparing the gene expression of IL-17A in the skin sample against a level of expression of IL-17A in a control skin sample of a healthy individual.

11. The method of claim 10, wherein the skin sample from the patient is from a patient suspected of having rosacea subtype III.

* * * * *